United States Patent [19]
Kagawa et al.

[11] Patent Number: 5,873,816
[45] Date of Patent: Feb. 23, 1999

[54] ELECTRONIC ENDOSCOPE HAVING AN INSERTIONAL PORTION A PART OF WHICH IS A CONDUCTIVE ARMOR

[75] Inventors: Hiroaki Kagawa, Sagamihara; Katsuyuki Saito, Hachioji; Hidetoshi Saito, Hanno, all of Japan; Nobuyuki Sakamoto, Hamburg, Germany

[73] Assignee: Olympus Optical Co., Ltd., Tokyo, Japan

[21] Appl. No.: 550,501

[22] Filed: Oct. 30, 1995

[30] Foreign Application Priority Data

| Nov. 2, 1994 | [JP] | Japan | 6-270046 |
| Nov. 8, 1994 | [JP] | Japan | 6-273868 |
| Nov. 10, 1994 | [JP] | Japan | 6-276733 |

[51] Int. Cl.$^6$ ........................................ A61B 1/05
[52] U.S. Cl. ................................ 600/134; 600/110
[58] Field of Search ........................ 600/109, 110, 600/134, 112, 139, 160; 348/65, 66, 71, 74, 75, 76

[56] References Cited

U.S. PATENT DOCUMENTS

| 4,677,471 | 6/1987 | Takamura et al. | 600/110 X |
| 4,879,992 | 11/1989 | Nishigaki et al. | 600/110 |
| 4,895,138 | 1/1990 | Yabe | 600/110 |
| 4,919,114 | 4/1990 | Miyazaki | 600/110 |
| 4,993,405 | 2/1991 | Takamura et al. | 600/110 |
| 5,569,158 | 10/1996 | Suzuki et al. | 600/110 |

FOREIGN PATENT DOCUMENTS

| 61-250608 | 11/1986 | Japan . |
| 63-270024 | 11/1988 | Japan . |

*Primary Examiner*—John P. Leubecker
*Attorney, Agent, or Firm*—Armstrong, Westerman, Hattori, McLeland & Naughton

[57] ABSTRACT

An electronic endoscope system comprises an insertional part at least part of whose armor is a conductor, an imaging unit incorporated in the insertional part and realized with a solid-state imaging device, a signal transmitting device for transmitting an electric signal that results from photoelectric conversion performed by the solid-state imaging device, and a signal processor for transforming an electric signal transmitted by the signal transmitting device into a video signal. The conductor serving as the armor of the insertional part is electrically isolated from the imaging unit, signal transmitting device, signal processor, and around.

26 Claims, 13 Drawing Sheets

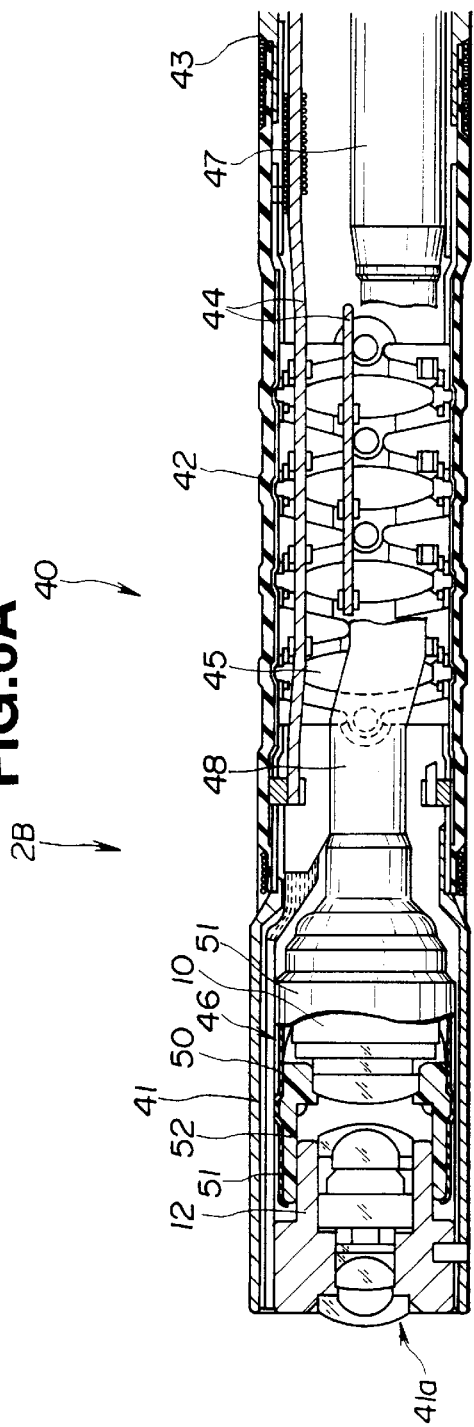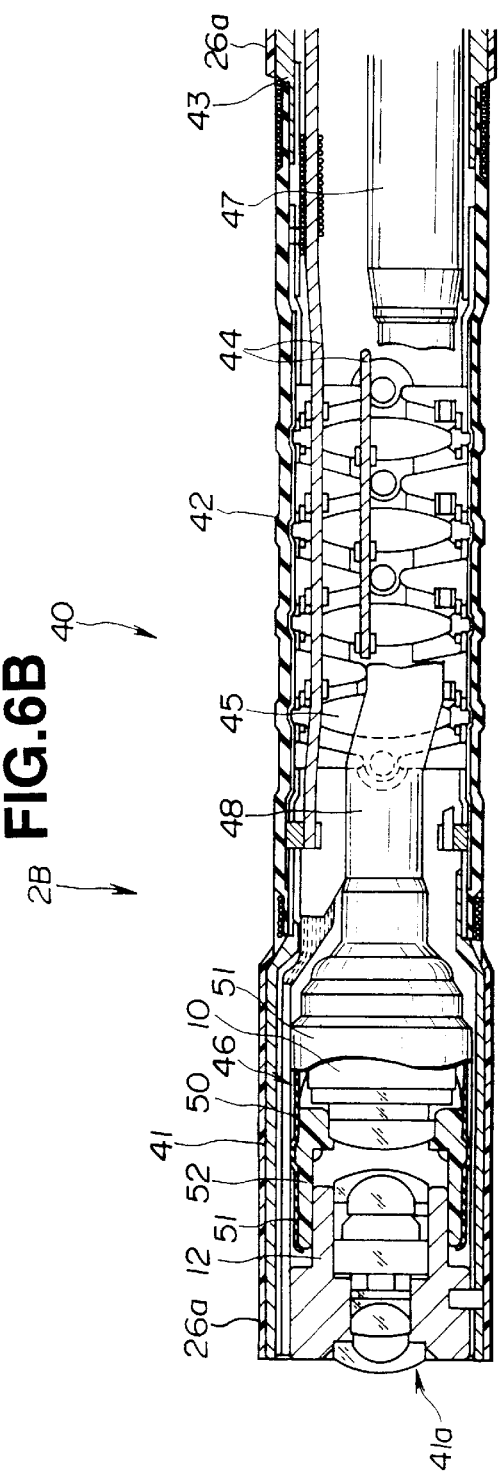

FIG.18
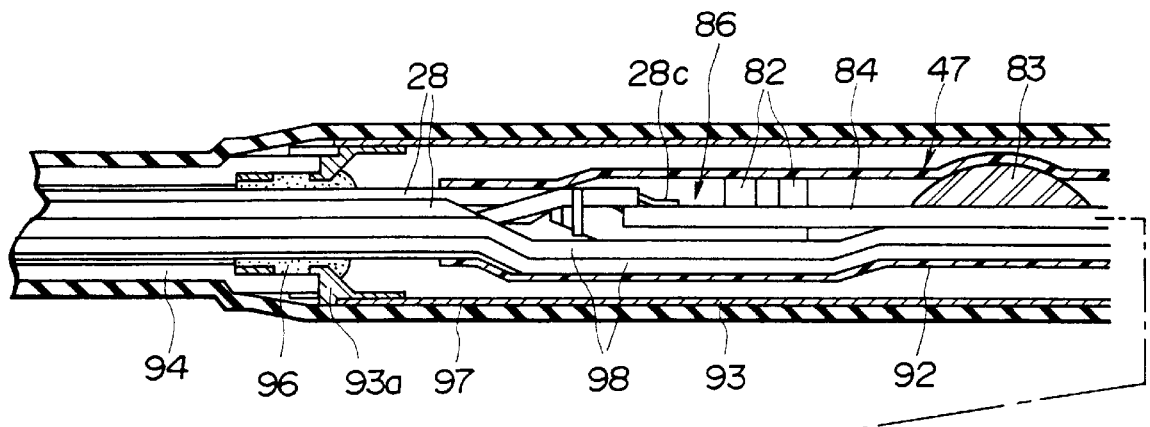
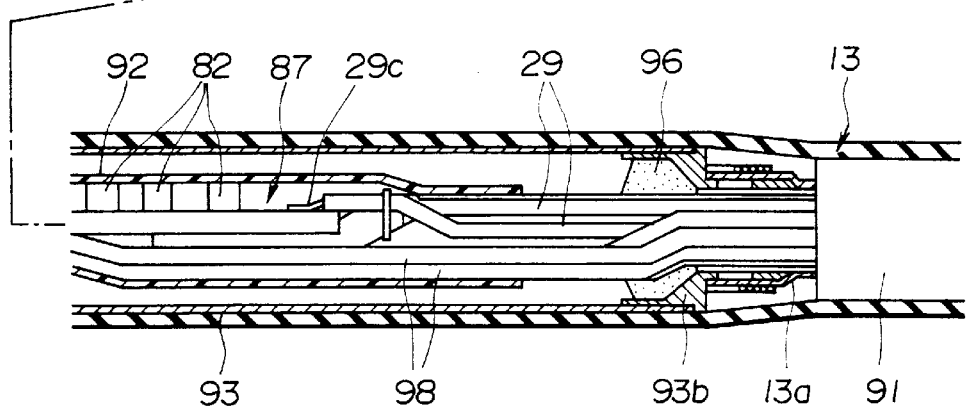
FIG.19
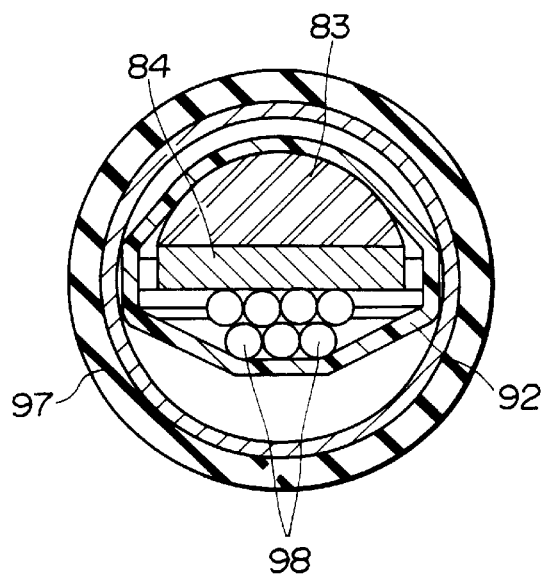

ELECTRONIC ENDOSCOPE HAVING AN INSERTIONAL PORTION A PART OF WHICH IS A CONDUCTIVE ARMOR

BACKGROUND OF THE INVENTION

1. Field of the Invention:

The present invention relates to an electronic endoscope system in which a solid-state imaging device is used as an imaging means and incorporated in an insertional part.

2. Description of the Related Art:

In recent years, an endoscope, of which elongated insertional part is inserted in a body cavity in order to observe an organ, or if necessary, of which therapeutic instrument channel is used to insert a therapeutic instrument for undertaking various kinds of therapy and treatment, has been adopted widely.

This kind of endoscope includes an electronic endoscope in which a solid-state imaging device such as a charge coupled device (hereinafter CCD) is used as an imaging means.

In the electronic endoscope, an optical image of an object is formed on an imaging surface of a solid-state imaging device via an objective optical system, the optical image formed on the imaging surface is converted into an electric signal, and then the electric signal resulting from photoelectric conversion is transmitted to a signal processing means by way of an electric signal transmitting means.

The signal processing means transforms the electric signal into a video signal. The video signal is then transmitted to a monitor unit, whereby the optical image of the object is displayed on a screen of the monitor unit for the purpose of observation.

When the electronic endoscope is used in combination with an external unit, for example, an electric equipment such as a high-frequency therapeutic instrument, a high-frequency noise radiating from the high-frequency therapeutic instrument is liable to mix with an electric signal that results from photoelectric conversion performed by the solid-state imaging device and is transmitted to the signal processing means. When the high-frequency noise mixes with an electric signal being transmitted to the signal processing means, the quality of an endoscopic image appearing on a screen of the monitor unit deteriorates markedly.

In an effort to prevent a noise from mixing with an electric signal, which results from photoelectric conversion performed by a solid-state imaging device, due to the use of an electric equipment in combination with an electronic endoscope having the solid-state imaging device, a conducting member is used as an armor of an insertional part of an endoscope. The conducting member is grounded via a ground in a signal processing means and thus shielded. Moreover, an isolation means is used to isolate the signal processing means from an external power supply means for supplying power to the signal processing means.

However, if the isolation between the signal processing means and external power supply means should become defective, there is a possibility that the conducting member serving as the armor of the insertional part of the electronic endoscope may conduct electricity to a ground in the power supply means. In the state in which the conducting member of the insertional part is conducting electricity to the ground, if a high-frequency therapeutic instrument is used, high-frequency current flows from the high-frequency therapeutic instrument to the conducting member serving as the armor of the insertional part of the electronic endoscope and realizing a shield. This causes high-frequency current to flow from the ground in the signal processing means toward the ground in the power supply means. At this time, if the conducting member serving as the armor of the insertional part is situated inside a body cavity, an unexpected burn may occur at a position in the body cavity near the conducting member.

In an electronic endoscope, a printed-circuit board on which an IC and other circuit elements are mounted and which realizes a signal processor is situated in the vicinity of a solid-state imaging device in order to process a signal acquired by the solid-state imaging device. For improving an signal-to-noise ratio, the printed-circuit board should be located near the solid-state imaging device. However, when an attempt is made to install both the solid-state imaging device and printed-circuit board in a distal portion of the endoscope, the distal portion must be made longer. This degrades the smoothness in inserting the endoscope into a body cavity.

Japanese Patent Laid-Open No. 61-250608 has disclosed an art in which a solid-state imaging device is incorporated in a first rigid unit in a distal portion of an insertional part, and a signal processor is incorporated in a second rigid unit situated in a proximal portion of the insertional part away from the first rigid unit.

In the signal processor disclosed in the unexamined publication, as shown in FIG. 1, center conductors 302 of signal cables 301 that are coaxial cables are attached to terminals 304 formed on a signal processor printed-circuit board 303 by performing soldering or the like. Outer conductors (shielded cables) 306 of the signal cables 301 are immobilized all together using a copper wire 307 and soldered to a conductive holder 305 to which the signal processor printed-circuit board 303 is fixed closely. Thus, the potentials at all the outer conductors 306 and holder 305 are equalized. This helps further stabilize shielding.

The terminals 304 are printed on the front side of the printed-circuit board 303, and extending to the end of the printed-circuit board for reasons of processing. The terminals 304 and outer conductors 306 may approach too closely each other at a junction 308 between the holder 305 and printed-circuit board 303 and then conduct electricity. If the terminals 304 and outer conductors 306 should conduct electricity, not only imaging is disabled but also a solid-state imaging device or signal processor is destroyed.

When an attempt is made to locate all the terminals 304 at substantially the same position, signal lines for inputting or outputting a video signal must be laid out over a longer distance. Electric noises originating from other terminals including a power supply terminal and other signal lines are liable to mix with a video signal. This results in deteriorated image quality.

When a solid-state imaging device and signal processor are separated from each other and linked by signal lines, the signal lines may distribute noises or may be susceptible to external noises. In the aforesaid structure, it is therefore requested to shorten the length of a distal rigid unit and improve shielding capability.

The solid-state imaging device incorporated in the first rigid unit is linked to the signal processor incorporated in the second rigid unit by signal lines that are routed through, for example, a bending section communicating the first rigid unit with the second rigid unit. When the bending section is angled, pulling force or compressing force works on the signal lines. This may cause a disconnection at a junction between the signal lines and solid-state imaging device or between the signal lines and signal processor.

Some of signals transferred between the solid-state imaging device and signal processing means are transmitted via the signal processor, while the others thereof are transmitted directly. In the structure in which the solid-state imaging device and signal processor are separated from each other, no consideration is taken into the signal lines directly linking the imaging device and signal processing means.

In an electronic endoscope, generally, not only an imaging unit but also a therapeutic instrument channel through which a light guide for transmitting illumination light or a therapeutic instrument is routed, and an aeration/affusion channel are formed in a distal portion. Japanese Unexamined Utility Model Publication No. 60-9041 has disclosed an art in which a light guide is installed so that the light guide can lie along the circumference of an imaging unit situated in a distal portion of an electronic endoscope. This structure contributes to an increase in amount of illumination light.

When the art disclosed in the utility model publication is adapted to an electronic endoscope, any of wires constituting the light guide may be broken. This results in a decreased amount of emitted light. In an effort to prevent the decrease in amount of emitted light, the light guide wires to be routed along the circumference of the imaging unit and extended toward the optimal portion of the endoscope are sheathed with a silicon tube or the like and thus bundled at the back end of the imaging unit in the distal portion of the endoscope distal to the bending section.

However, as shown in FIG. 2, when a light guide 313 lying along the circumference of an imaging unit 312 incorporated in a distal structure 311 of an endoscope 310 is extended toward the proximal portion of the endoscope, the portion of the endoscope sheathed with a silicon tube 317 is sandwiched between a junction 315, at which the distal structure 311 is joined with the distal end of a bending section 314, and a signal cable 316 extending from the imaging unit 312 because of a narrow space A between the junction 315 and the signal cable 316. In this situation, if angling is repeated, any of the wires constituting the light guide located near the silicon tube in the space A may be broken.

For preventing the light guide 313 from being broken in the distal structure, it is essential to widen the space A between the junction 315 and signal cable 316. If the outer diameter of the distal structure 311 is made larger in order to ensure a wide space, it contradicts the concept that the diameter of an insertional part of an endoscope is decreased in an effort to alleviate patient discomfort occurring at the time of inserting the insertional part into a body cavity.

OBJECTS AND SUMMARY OF THE INVENTION

An object of the present invention is to provide an electronic endoscope system characteristic of high safety ensured by preventing occurrence of an unexpected burn caused by a conducting member serving as an armor of an insertional part to be inserted in a body cavity.

Another object of the present invention is to provide an electronic endoscope system capable of preventing irradiation of noises from an inside of the electronic endoscope and deterioration in image quality due to the influence of noises originating from an external unit.

Yet another object of the present invention is to provide an electronic endoscope system in which terminals on a signal processor printed-circuit board and outer conductors of a signal cable will not conduct electricity, and an imaging means or signal processor will not be destroyed.

Still another object of the present invention is to provide an electronic endoscope system in which a solid-state imaging device and signal processor are separated from each other and a signal cable linking the solid-state imaging device and signal processor is routed through a bending section, and of which durability against angling has improved.

Another object of the present invention is to provide an electronic endoscope in which although the diameter of a distal portion of an endoscope is not made larger, a light guide lying along the circumference of an imaging unit can be smoothly extended toward the distal portion of the endoscope.

Briefly, an electronic endoscope system of the present invention comprises an insertional part at least part of whose armor is formed with a conducting member, an imaging means incorporated in the insertional part and realized with a solid-state imaging device, a signal transmitting means for transmitting an electric signal that results from photoelectric conversion performed by the solid-state imaging device, and a signal processing means for transforming an electric signal transmitted by the signal transmitting means into a video signal. The conducting member serving as the armor member of the insertional part, imaging means, signal transmitting means, and signal processing means are electrically isolated mutually.

BRIEF DESCRIPTION OF THE DRAWINGS

FIG. 1 is an explanatory diagram showing a connected state of a signal cable with terminals formed on a printed-circuit board;

FIG. 2 is a sectional view showing a positional relationship between an imaging unit and light guide in a distal portion of an endoscope;

FIG. 3 is an explanatory diagram schematically showing the configuration of an electronic endoscope system;

FIG. 4A is an explanatory diagram showing an electronic endoscope, in which an armor of an insertional part is formed with a rigid metallic member, and a signal processing means;

FIG. 4B is an explanatory diagram showing an electronic endoscope in which an insulation layer is formed along the outer circumference of a rigid metallic member serving as the armor of the insertional part shown in FIG. 4A;

FIG. 6A is a sectional view showing the structure of an insertional part of an electronic endoscope in accordance with the third embodiment of the present invention, wherein the armor of the insertional part is formed with a rigid metallic member and the insertional part has a bending section;

FIG. 6B is a sectional view showing the insertional part of the electronic endoscope in which an insulation layer is formed along the outer circumference of a rigid metallic member serving as the armor of the insertional part shown in FIG. 6A;

FIG. 7 is a sectional view schematically showing the structure of an imaging unit;

FIG. 8 is an explanatory diagram showing the arrangement of a signal processor printed-circuit board and a signal cable;

FIG. 9 is an explanatory diagram showing an attached state of a signal cable to terminals;

FIG. 14 shows a layout of electric parts on an upper layer of the two-layer printed-circuit board;

FIG. 15 shows a layout of electric parts on a lower layer of the two-layer printed-circuit board;

FIG. 16 shows a section of an insertional part in a longitudinal direction of an electronic endoscope;

FIG. 17 shows a section of a proximal rigid unit perpendicular to the longitudinal direction of the electronic endoscope;

FIGS. 18 and 19 relate to the ninth embodiment;

FIG. 18 is an enlarged view showing electric parts stowed in a proximal rigid unit and their surroundings;

FIG. 19 shows a section of the proximal rigid unit containing electric parts perpendicular to a longitudinal direction of an endoscope;

FIG. 20 is a perspective view schematically showing the structure of a distal portion of an electronic endoscope;

FIG. 21 is a perspective view showing the distal portion of the electronic endoscope;

FIG. 22 is a sectional view showing the structure of the distal portion of the electronic endoscope.

DETAILED DESCRIPTION OF THE PREFERRED EMBODIMENTS

Embodiments of the present invention will be described with reference to the drawings.

Figure 3:
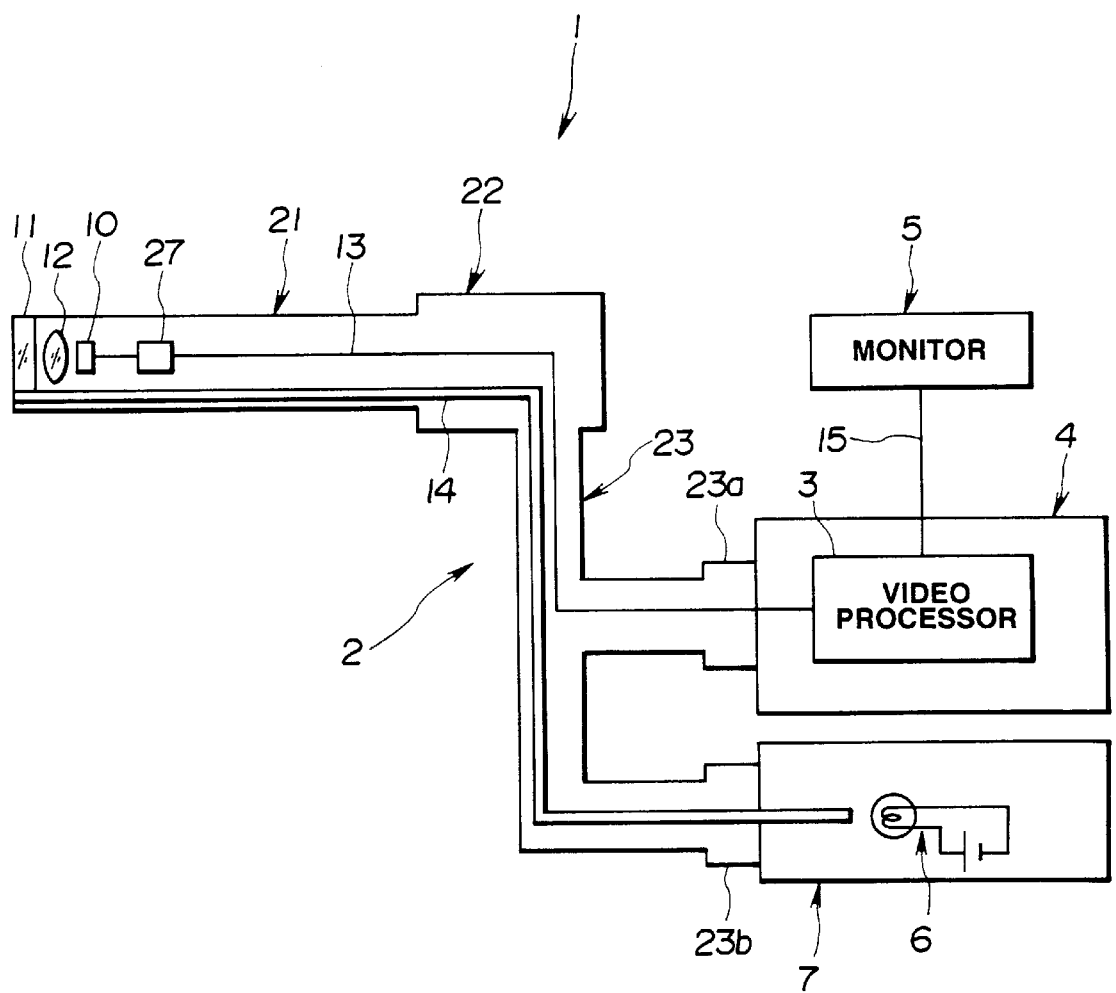
FIGS. 3 and 4 relate to the first embodiment of the present invention.
Figure 4:
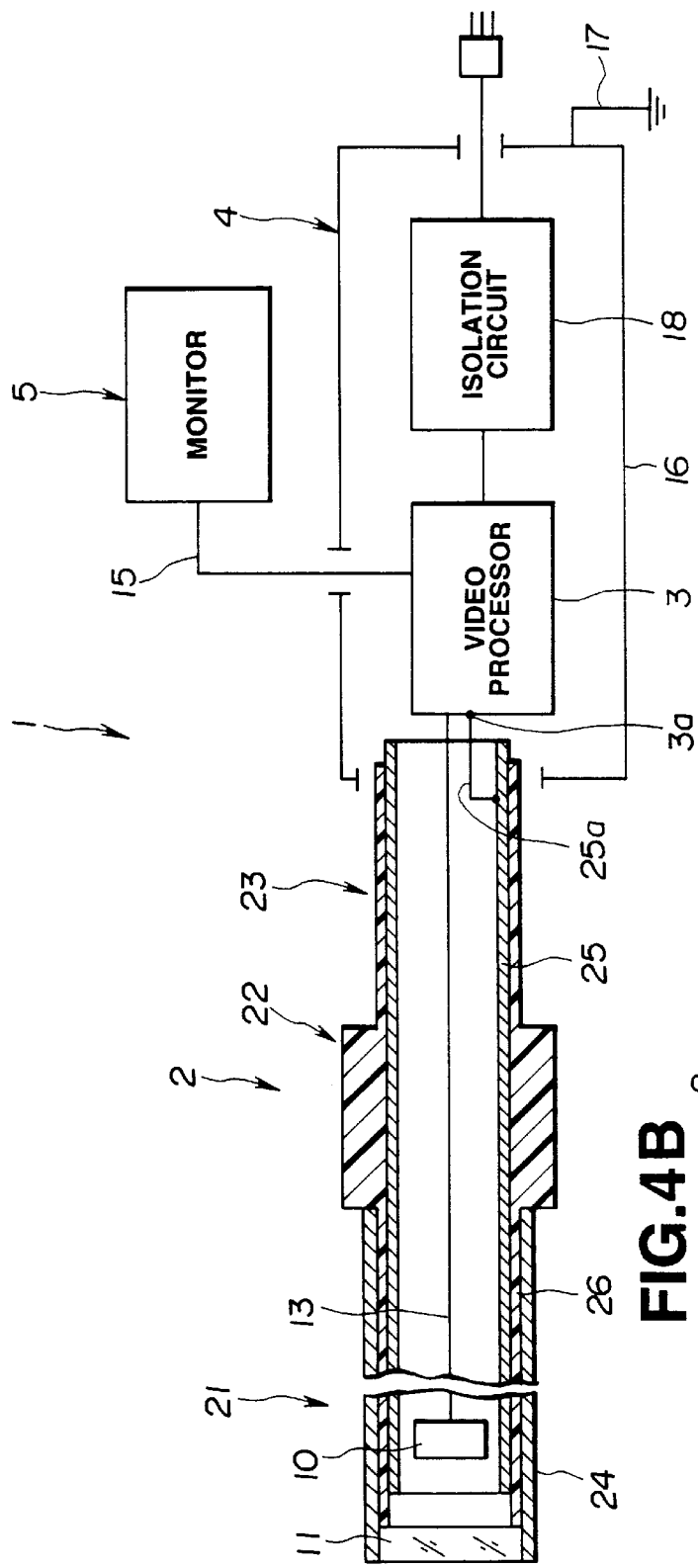

Referring to FIGS. 3 and 4, the first embodiment of the present invention will be described.

As shown in FIG. 3, an electronic endoscope system 1 of this embodiment consists mainly of an electronic endoscope 2 in which a solid-state imaging device serving as an imaging means; such as, a CCD is incorporated in a portion distal to an insertional part 21, a camera control unit (hereinafter CCU) 4 including a video processor 3 that serves as a signal processing means for transforming an electric signal sent from the CCD 10 in the electronic endoscope 2 into a video signal, a monitor 5 connected to the CCU 4 and designed to display a video signal sent from the video processor 3 as an endoscopic image, and a light source unit 7 including a light source 6 for supplying illumination light to the electronic endoscope 2.

An objective optical system 12 for converging an object image on an imaging surface of the CCD 10 is located behind a lens cover 11 in the distal portion of the insertional part 21. An electric signal resulting from photoelectric conversion performed by the CCD 10 and a signal processor printed-circuit board 27 containing a signal processor is transmitted to the video processor 3 over a signal cable 13 serving as a signal transmitting means that lies through the insertional part. Light guide fibers 14 for illuminating an object by irradiating illumination light from the distal surface of the insertional part are routed through the insertional part 21.

A grip 22-communicates with the proximal end of the insertional part 21 of the electronic endosdope 2. A universal cord 23 containing the signal cable 13 and light guide fibers 14, which lie through the insertional part 21 and grip 22 and extend to the CCU 4 and light source unit 7, is extending from the grip 22. The universal cord 23 has connectors 23a and 23b. The connectors 23a and 23b are detachably coupled to the CCU 4 and light source unit 7.

Illumination light emanating from the light source 6 in the light source unit 7 propagates over the light guide fibers 14, and comes out of the distal end of the insertional part so as to illuminate an object. An optical image of the object illuminated by the illumination light is relayed by the objective optical system 12 in the insertional part 21 and converged on the imaging surface of the CCD 10. The optical image converged on the imaging surface of the CCD 10 is converted into an electric signal, and then transmitted to the CCU 4 by way of the signal cable 13. The electric signal is transformed into a video signal by the video processor 3 in the CCU 4, and sent to a monitor 5 over a video cable 15. Consequently, an endoscopic image is displayed on a screen of the monitor 5.

As shown in FIG. 4A, the armor of the insertional part 21 distal to the grip 22 of the electronic endoscope 2 is a metallic pipe 24 formed with a rigid conducting member, for example, a metallic member.

In the metallic pipe 24 serving as the armor of the insertional part 21, the CCD 10 and signal cable 13 are enclosed with a shield member 25 that is a metallic tube or braided tube formed with a conducting member. The shield member 25 is realized as a shield by coupling a ground line 25a to a ground 3a of the video processor 3. That is to say, the potential at the shield member 25 is retained at a ground level as it is in the video processor 3.

An insulator 26, the grip 22, and the universal cord 23, each of which is realized with an insulating member made of ceramic or fluorocarbon resin, are formed over the outer circumference of the shield member 25. By forming the insulator 26 over the outer circumference of the shield member 25, not only the shield member 25 and a metallic housing 16 of the CCU 4 are electrically isolated from each other but also the metallic pipe 24 and shield member 25 are electrically isolated from each other. The metallic pipe 24 constituting the insertional part 21 is electrically perfectly isolated from the shield member 25 and the metallic housing 16 of the CCU 4. In FIG. 4, the insulator 26, grip 22, and universal cord 23 are depicted as a united body. This is intended to indicate that the insulator 26, grip 22, and universal cord 23 are insulating members.

The metallic housing 16 that is the housing of the CCU 4 is connected to a mains ground by way of a ground line 17. The ground 3a of the video processor 3 is therefore floating relative to the mains ground. Power is supplied from the mains to the video processor 3 with the video processor 3 electrically isolated by the isolation circuit 18. The metallic pipe 24 constituting the insertional part 21 of the electronic endoscope 2 is floating relative to the video processor 3 and mains.

Since the electronic endoscope system 1 has the aforesaid configuration, not only the metallic pipe 24 serving as the armor of the insertional part 21 of the electronic endoscope 2 is insulated from the video processor by means of the insulator 26 but also the video processor 3 is insulated from the mains by means of the isolation circuit 18. Thus, the electronic endoscope system 1 is insulated from the mains ground on a dual basis. If insulation of the metallic pipe 24 from the video processor 3 or insulation of the video processor 3 from the mains should become defective, an operator may be unaware of the fact and therefore operate an electric equipment such as a high-frequency therapeutic instrument. In this case, if high-frequency current should flow into the metallic pipe serving as the armor of the insertional part of the electronic endoscope, the high-frequency current will not flow into the mains ground. An unexpected burn attributable to the metallic pipe 24 will therefore not occur.

As shown in FIG. 4B, when the electronic endoscope 2 has an insulator 26a formed, as mentioned above, along the outer circumference of the rigid metallic pipe 24 serving as the armor of the insertional part 21, if the insulator 26a formed along the outer circumference of the metallic pipe 24 should peel off to bare the metallic surface of the metallic pipe 24, high-frequency current will not flow into the mains ground. An unexpected burn attributable to the metallic pipe 24 will not occur.

As mentioned above, an insulator is interposed between a metallic pipe serving as an armor of an insertional part and a shield member for shielding a CCD and signal cable. In addition, an insulating member is used to construct an operation unit situated at a proximal end of the insertional part. The metallic pipe of the insertional part can therefore be made floating.

The shield member for an electronic endoscope and a video processor in a CCU are linked by a ground line. This structure can prevent a high-frequency noise radiating from a high-frequency therapeutic instrument from mixing with an electric signal resulting from photoelectric conversion performed by the CCD and being transmitted to a signal processing means. Deterioration in quality of an endoscopic image appearing on a screen of a monitor unit, which is caused by a noise radiating from an electric equipment and mixing with an electric signal sent from the signal processing means, will not occur.

Figure 5:
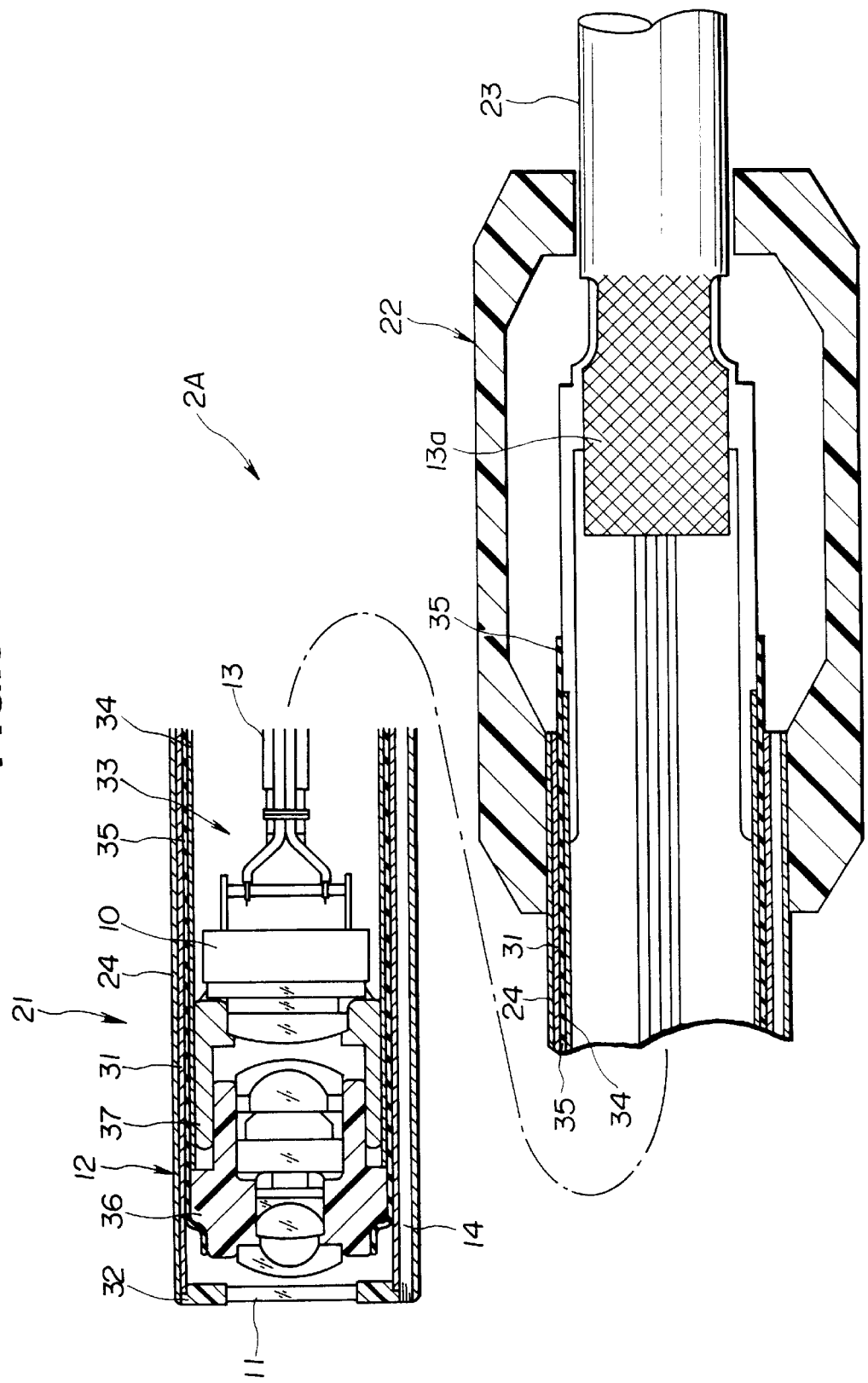
FIG. 5 is a sectional view showing the structures of an insertional part and grip of an electronic endoscope in accordance with the second embodiment of the present invention.

Referring to FIG. 5, the second embodiment of the present invention will be described.

As illustrated, the insertional part 21 of an electronic endoscope 2A of this embodiment comprises the metallic pipe 24 that is a rigid conducting member, and a second metallic pipe 31 inserted in the metallic pipe 24. The light guide fibers 14 for supplying illumination light are placed in a space created between the second metallic pipe 31 and metallic pipe 24. A distal member 32 is situated at the distal end of the insertional part 21. A lens cover 11 is joined with the distal member 32.

An imaging unit 33 is placed in the second metallic pipe 31. The imaging unit 33 consists of the objective optical system 12 composed of a plurality of optical lenses and situated in a unit tube 34 serving as a third metallic pipe formed with a conducting member, and the CCD 10 located behind the objective optical system 12. The signal cable 13 for use in driving the CCD 10 or transmitting a signal is extending from behind the CCD 10.

The proximal end of the unit tube 34 conducts electricity to a general shield 13a joined with the signal cable 13 in the grip 22, thus realizing a shield. The outer circumference of the unit tube 34 is covered with a thermo-contractive tube 35 that is an insulating member made of fluorocarbon resin or the like, whereby the unit tube 34 is insulated from the second metallic pipe 31 and metallic pipe 24 constituting the insertional part 21.

The objective optical system 12 lying in the distal portion of the unit tube 34 has the plurality of optical lenses locked in an objective lens frame member 36 formed with an insulating member made of a resin or ceramic. A metallic locking frame member 37 lying behind the objective lens frame member 36 is locked in the distal portion of the unit tube 34. A thermo-contractive tube 35 is routed to the distal portion of the objective lens frame member 36 in order to shield the outer circumference of the distal portion thereof and overlap the unit tube 34. Thus, reliable insulation is accomplished with a sufficient creepage distance ensured between the second metallic pipe 31 and metallic pipe 24, and the unit tube 34.

The grip 22 joined with the proximal end of the insertional part 21 is formed with a resin member having an insulating ability, and thus insulated from the metallic pipe 24 and second pipe 31, which are conducting members, constituting the insertional part 21. The thermo-contractive tuber 35 overlaps the unit tube 34 by a given length within the grip 22 in the same manner as it does in the distal portion of the insertional part 21, so that reliable insulation can be accomplished with a sufficient creepage distance ensured between the second metallic pipe 31 and metallic pipe 24, and the unit tube 34.

The universal cord 23 whose skin made of silicon or polyvinyl chloride insulates and shields the outside of the general shield 13a is extending from the back end of the grip 22. The other members having the same structures as those in the first embodiment are assigned the same reference numerals. The description of the members will be omitted.

As mentioned above, a n imaging unit made by stowing an objective optical system and imaging means in a unit tube that is a conducting member is placed in an insertional part whose armor is a conducting member. When the unit tube is sheathed with a thermo-contractive tube, the distal portion of the thermo-contractive tube is stretched over an insulating objective lens frame member situated in the distal portion of the unit tube. Besides, the proximal portion of the thermo-contractive tube overlaps the unit tube by a given length in a grip so that a sufficient creepage distance can be ensured between the second metallic pipe 31 and metallic pipe 24, and the unit tube. Thus, the conducting members realizing the unit tube and insertional part are insulated. The other effects and advantages are identical to those of the first embodiment.

Referring to FIG. 6A, the third embodiment of the present invention will be described.

As shown in FIG. 6A, an insertional part 40 of an electronic endoscope 2B of this embodiment is made by joining a distal rigid unit 41 formed with a metallic pipe that is a rigid conducting member, a bending section 42 made by concatenating a plurality of bending tops, and a proximal rigid unit 43 formed with a metallic pipe that is a rigid conducting member in that order from the distal portion of the insertional part 40.

Angle wires 44 for angling the bending section 42 vertically or laterally are lying through the insertional part 40. The angle wires 44 are coupled to an angle lever formed in an operation unit (grip). By operating the angle lever, the angle wires 44 are advanced or withdrawn in order to angle the bending section 42 in any vertical or lateral direction. A distal surface 41*a* of the distal rigid unit 41 is thus oriented in any desired direction.

An imaging unit 45 is incorporated in the insertional part 40. In the imaging unit 45, a distal unit part 46 composed of the objective optical system 12 and CCD 10 is stowed in the distal rigid unit 41, and a back unit part 47 for transmitting an electric signal, which results from photoelectric conversion performed by the CCD 10 and processed by a signal processor is stowed in the proximal rigid unit 43. Inside the bending section 42, a connection cable 48 links the CCD 10 and signal processor in the back unit part 47 and carries a driving signal for driving the CCD 10 and an electric signal.

The imaging unit 45 incorporated in the insertional part 40 is, similarly to the ones of the aforesaid embodiments, covered with a shield member 50 that is a braided tube or shield mesh formed with a conducting member. The outer circumference of the shield member 50 is covered with a thermo-contractive tube 51 made of a flexible material, for example, polyolefine. Owing to this structure, the imaging unit 45 is insulated against the distal rigid unit 41 and proximal rigid unit 43 that are conducting members constituting the insertional part 40.

The thermo-contractive tube 51 stretches over a locking frame member 52 that is an insulating member fixed to the distal end of the shield member 50 as part of the shield member 50. Similarly to the second embodiment, reliable insulation can be accomplished with a sufficient creepage distance ensured between the distal rigid unit 51 and imaging unit 45.

The grip (operation unit) 22 is, similarly to the one in the previous embodiment, joined with the proximal end of the insertional part 40. A universal cord extending from the grip is coupled to each of a light source unit and a CCU. Alternatively, as shown in FIG. 6B, the insulator 26*a* may be, as it is in the first embodiment, formed along each of the outer circumferences of the distal rigid unit 41 and proximal rigid unit 43 of the insertional part 40 of the electronic endoscope 2B having the bending section 42. The other members having the same structures as those in the previous embodiment are assigned the same reference numerals. The description of the members will be omitted.

As mentioned above, an imaging unit is divided into a distal unit part and a back unit part. The distal unit part and back unit part are linked by a connection cable. This structure contributes to a decrease in length of a distal rigid unit of an electronic endoscope. The other effects and advantages are identical to those of the aforesaid embodiments.

Figure 7:
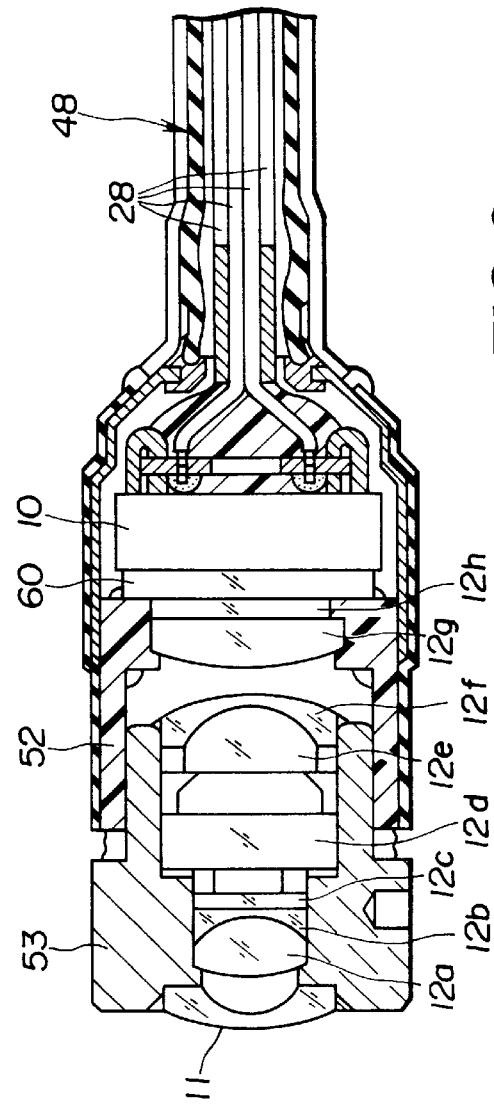
FIGS. 7 to 9 relate to the fourth embodiment of the present invention.
Figure 8:
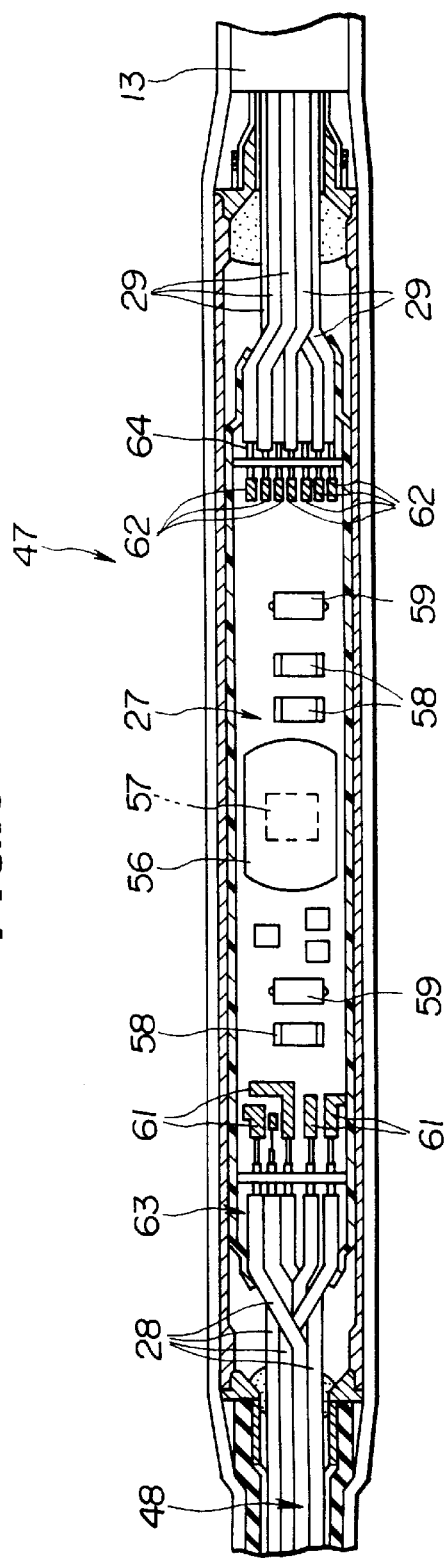

Referring to FIGS. 7 to 8, the fourth embodiment of the present invention will be described.

In an electronic endoscope of this embodiment, terminals on a signal processor printed-circuit board and outer conductors of a signal cable do not conduct electricity, and therefore a solid-state imaging device and signal processor will not be destroyed.

As shown in FIG. 3, the signal processor printed-circuit board 27 (hereinafter, printed-circuit board 27) containing a signal processor is incorporated in the distal portion of the insertional part 21.

As shown in FIGS. 7 and 8, the printed-circuit board 27 and CCD 10 are linked by a connection cable 48 composed of a plurality of signal lines 28. The signal cable 13 for inputting or outputting a signal to or from the printed-circuit board 27 is coupled with the proximal end of the printed-circuit board 27.

As shown in FIG. 7, the objective optical system 12 is made by arranging a convex lens 12*a*, concave lens 12*b*, flat lens 12*c*, flat lens 12*d*, convex lens 12*e*, and concave lens 12*f* in an objective lens frame member 53, of which inner surface is blackened, in that order form the distal end of the objective optical system 12. The proximal portion of the objective lens frame member 53 is enclosed with a locking frame member 52 made of black plastic. In the locking frame member 52, a convex lens 12*g* and flat lens 12*h* are locked in that order from the distal end of the locking frame member 52. A cover glass 60 fixed to the front side of the CCD 10 is attached to the proximal end of the flat lens 12*h*.

As shown in FIG. 8, the connection cable 48 coupled to a proximal terminal or the like of the CCD 10 has the plurality of signal lines 28 thereof soldered and fixed to distal terminals 61 on the printed-circuit board 27. On the printed-circuit board 27, a signal processing IC (hereinafter an HIC) 57 constituting a signal processor is mounted firmly. The HIC 57 is coated with a filler 56 facilitating heat dissipation and electric insulation. On the printed-circuit board 27, capacitors 58, resistors 59, and other electric parts which constitute a signal processor are mounted firmly. These electric parts are formed in such a way a pattern of printed wiring will become as short as possible in order to prevent mixing of noises. The capacitors 58, resistors 59, and other electric parts to be mounted on the printed-circuit board are therefore arranged with the longitudinal directions thereof made perpendicular to the longitudinal direction of the printed-circuit board. Signal lines 29 constituting the signal cable 13 are soldered to proximal terminals 62 on the printed-circuit board 27.

Figure 9:
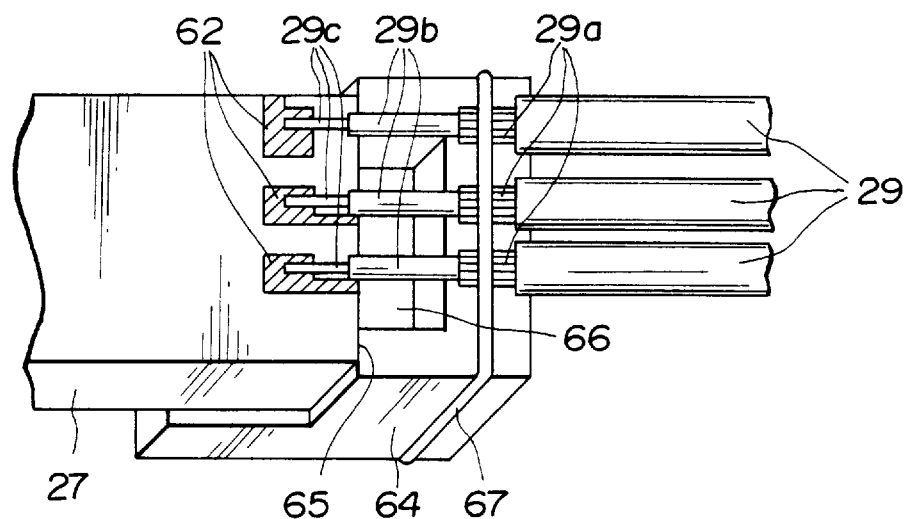

Referring to FIG. 9, the connection between the printed-circuit board and a holder will be described. The connection between the printed-circuit board 27 and a distal holder 63 is identical to the one between the printed-circuit board 27 and a proximal holder 64. Only the connection between the printed-circuit board 27 and proximal holder 64 will be described, but the connection between the printed-circuit board 27 and distal holder 63 will not.

As illustrated, the proximal holder 64 holding the proximal portion of the printed-circuit board 27 is formed with a conducting member and fixed closely to the end surface of the printed-circuit board 27. A junction 65 between the proximal holder 64 and printed-circuit board 27 is realized solely with a margin of a proximal end of the printed-circuit board 27. The center of the end of the printed-circuit board 27 is not in contact with the proximal holder 64 because of a ditch 66 formed in the proximal holder 64.

The signal lines 29 have outer conductors 29*a* thereof bared at the proximal end of the proximal holder 64. The outer conductors 29*a* are bound to the proximal holder 64 all together by winding a copper wire 67 about the proximal holder 64. The copper wire 67 and outer conductors 29*a* are electrically coupled with one another by soldering.

The outer conductors 29*a* are discontinued at a position on the ditch 66 of the proximal holder 64, thus baring inner insulators 29*b* of the outer conductors 29*a*. Center conductors 29*c* inside the insulators 29*b* are bared on proximal terminals 62 and fixed to the proximal terminals 62 by soldering.

The distal terminals 61 and proximal terminals 62 are electrodes printed on the front side of the printed-circuit board 27. The pattern of printed wiring stretches over in the inside of the printed-circuit board 27.

As mentioned above, signal lines are passed over a ditch formed in a holder and then fixed to terminals on a printed-circuit board. The terminals on the printed-circuit board are therefore separated from outer conductors of the signal lines by the ditch in the holder. A copper wire used to cause all the outer conductors to conduct is retained away from the terminals. Since the ditch is formed in the holder to which the end of the printed-circuit board is fixed closely, the terminals along the edge of the printed-circuit board are separated from the outer conductors and the copper wire combining the outer conductors. Destruction of a CCD or printed-circuit board attributable to the fact that the outer conductors conduct electricity to the terminals can therefore be prevented.

Electric parts mounted on the printed-circuit board are arranged with the longitudinal directions thereof made perpendicular to the longitudinal direction of the printed-circuit board. The longitudinal dimension of the printed-circuit board and the length of the pattern of printed wiring on the board can therefore be minimized, whereby mixing of noises can be suppressed.

Figure 10:
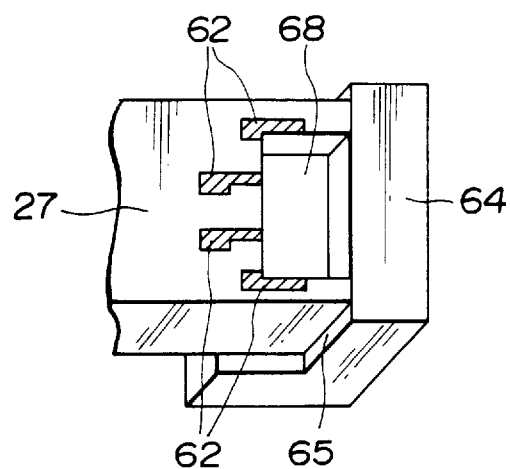
FIG. 10 is an explanatory diagram showing a variant of a signal processor printed-circuit board in accordance with the fourth embodiment of the present invention.

Alternatively, a ditch 68 may be formed in the printed-circuit board as shown in FIG. 10. The terminals 62 may be formed along the margin of the ditch 68. This alternative provides the same effects and advantages as the fourth embodiment. A variant in which a ditch is formed in each of the holder and printed-circuit board is also conceivable.

Figure 11:
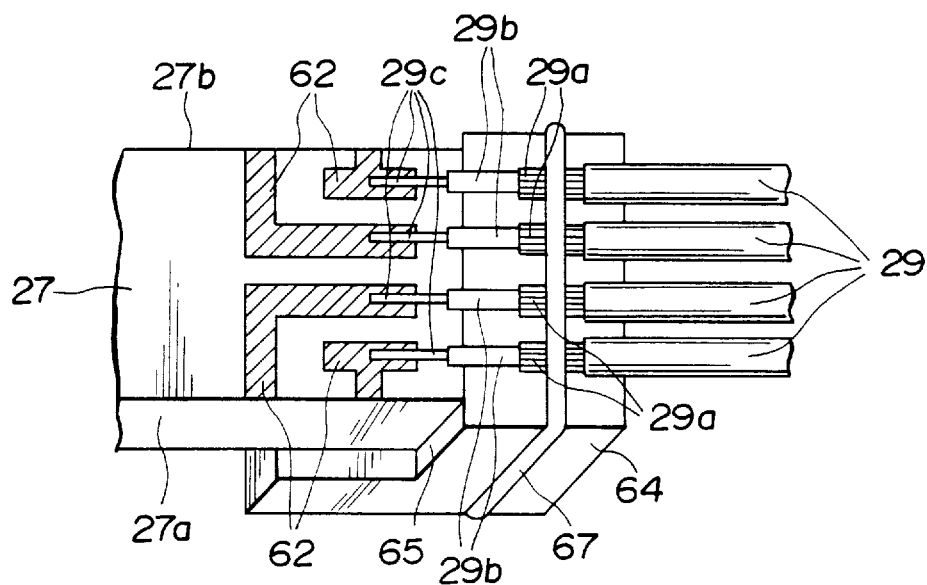
FIG. 11 is an explanatory diagram showing an attached state of a signal cable to terminals in the fifth embodiment of the present invention.

Referring to FIG. 11, the fifth embodiment of the present invention will be described.

As illustrated, in this embodiment, the ends of the proximal terminals 62 on the printed-circuit board 27 are not extended toward the proximal holder 64 but bifurcated toward lateral sides 27a and 27b of the printed-circuit board 27. The end of the proximal holder 64 is in contact with the proximal end of the printed-circuit board 27. The other members having the same structures and effects as those in the fourth embodiment are assigned the same reference numerals. The description of the members will be omitted.

According to the foregoing structure, the ends of the proximal terminals 62 on the printed-circuit board 27 are not extended toward the proximal holder 64 but bifurcated toward the lateral sides 27a and 27b of the printed-circuit board 27. The ends of the proximal terminals 62 do not therefore touch either the proximal holder 64 or the outer conductors 29a of the signal lines 29.

As mentioned above, in this embodiment, outer conductors will not conduct electricity to terminals. Imaging will not be disabled, and a CCD or printed-circuit board will not be destroyed. Moreover, since a holder need not be subjected to any special machining, an inexpensive electronic endoscope can be provided.

Figure 12:
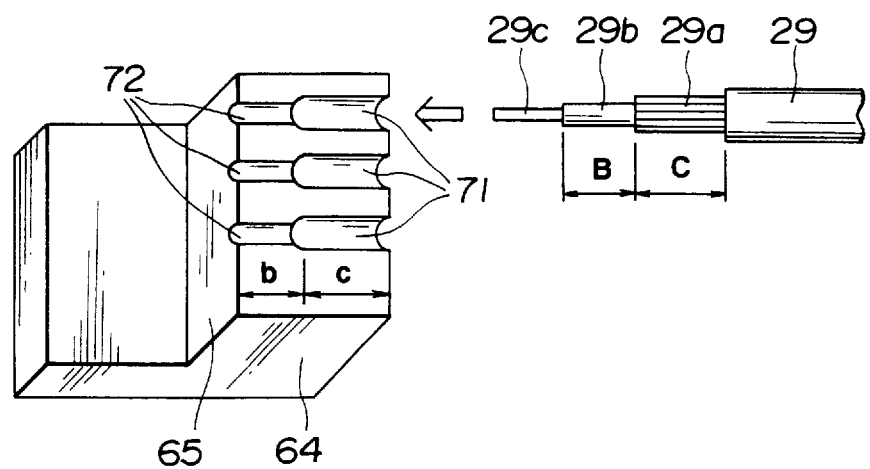
FIG. 12 is an explanatory diagram showing an attached state of a signal cable to terminals in the sixth embodiment of the present invention.

Referring to FIG. 12, the sixth embodiment of the present invention will be described.

As illustrated, in this embodiment, large-diameter ditches 71 for stowing the outer conductors 29a of the signal line 29 and small-diameter ditches 72 for stowing the insulators 29b are formed from the proximal end of the proximal holder 64 toward the junction 65 with the printed-circuit board 27.

The large-diameter ditches 71 have a slightly larger outer diameter than the outer conductors 29a. Likewise, the small-diameter ditches 72 have a slightly larger outer diameter than the insulators 29b. An axial length B of each insulator 29b is slightly longer than an axial length b of each small-diameter ditch 72. The large-diameter ditches 71 have a larger diameter than the small-diameter ditches 72. The diameters of the small-diameter ditches 72 are larger than those of the outer conductors 29a. The outer conductors 29a will therefore not touch the printed-circuit board 27.

Figure 1:
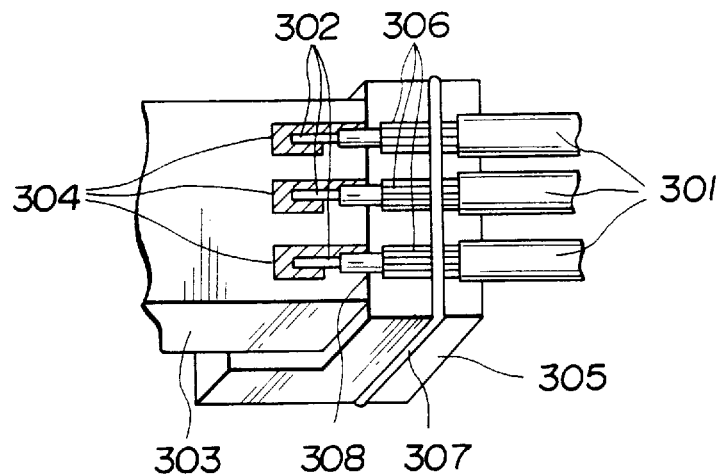
FIGS. 1 and 2 relate to a prior art.

After positioned to the large-diameter ditches 71, the outer conductors 29a are fixed to the proximal holder 64 by soldering. The printed-circuit board to be fixed to the holder of this embodiment includes the one shown in FIG. 9, the one shown in FIG. 11, and the one shown in FIG. 1.

As mentioned above, outer conductors of signal lines will not touch terminals on a printed-circuit board. Imaging will therefore not be disabled, and a CCD or printed-circuit board will not be destroyed. Moreover, since binding by a copper wire employed in the fourth and fifth embodiments becomes unnecessary, an inexpensive electronic endoscope can be provided.

Figure 13:
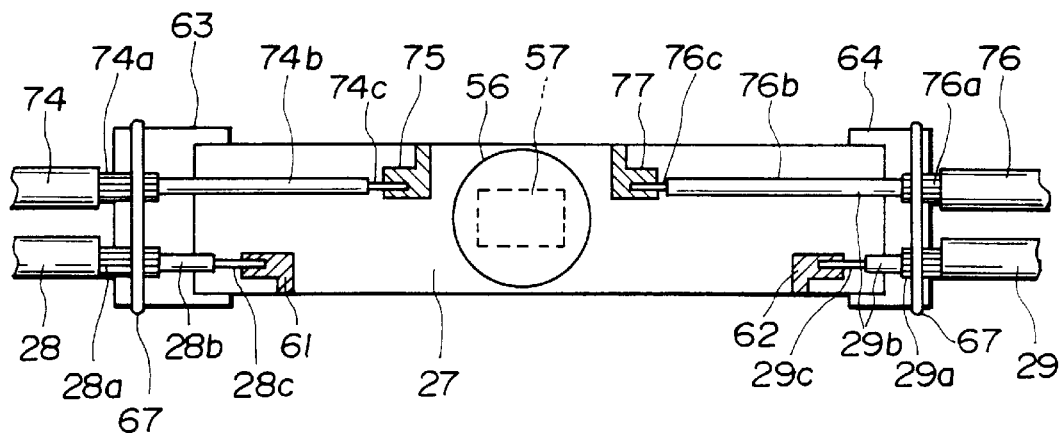
FIG. 13 is an explanatory diagram showing an attached state of a signal cable to terminals in the seventh embodiment of the present invention.

Referring to FIG. 13, the seventh embodiment of the present invention will be described.

In an electronic endoscope of this embodiment, video signal input/output terminals of a signal processor are unsusceptible to noises originating from other terminals.

A video cable 74 extending from the CCD 10 has, similarly to, for example, the signal lines 28 for supplying power, outer conductors 74 thereof bared on the distal holder 63. The bared outer conductors 74 are bound together with the outer conductors 29a of the signal lines 29 by the copper wire 67. Insulators 74b of the video cable 74 are extended to the vicinity of a video input terminal 75 formed near the HIC 57, and center conductors 74c thereof are fixed to the video input terminal 75 by soldering.

The same applies to a video cable 76 coupled to the proximal end of the printed-circuit board 27. That is to say, outer conductors 76a of the video cable 76 are, similarly to, for example, those of the signal lines 29 for supplying power, bared on the proximal holder 64, and bound together with the outer conductors 29a of the signal lines 29 by the copper wire 67. Insulators 76b of the video cable 76 are extended to the vicinity of a video output terminal 77 near the HIC 57, and center conductors 76c thereof are fixed to the video output port 77 by soldering.

Since the printed-circuit board 27 has the foregoing structure, the distances from a position at which the signal lines constituting the video cables 74 and 76 are bared to the position of the HIC 57 are very short. The bared signal lines of the video cables 74 and 76 extending to the HIC 57 on the printed-circuit board 27 are therefore very short. Electric noises originating from the other signal lines 28 and 29 are hardly picked up.

As mentioned above, in this embodiment, noises from other signal lines hardly enter video cables. The quality of an endoscopic image appearing on a screen of a monitor unit does not deteriorate.

Figure 14:
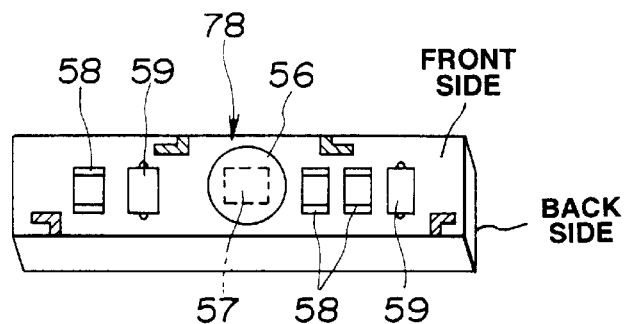
FIGS. 14 and 15 relate to a two-layer printed-circuit board.
Figure 15:
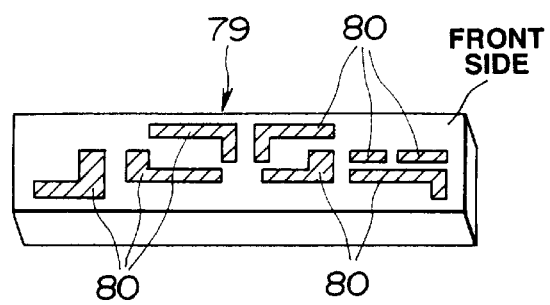

In the aforesaid embodiment, the printed-circuit board 27 may have a two-layer structure consisting of upper and lower layers as shown in FIGS. 14 and 15. Specifically, as shown in FIG. 14, the front side of an upper layer 78 is regarded as a surface on which the HIC 57, capacitors 58, resistors 59, and others are mounted. The front side of a lower layer 79 is, as shown in FIG. 15, regarded as a surface containing a pattern of circuits 80 alone. The back side of the upper layer 78 and the front side of lower layer 79 are attached to each other, thus constructing a signal processor printed-circuit board. According to this structure, conductors including dust and moisture will not enter the pattern of circuits 80. The capability of a signal processor will not be impaired.

Figure 16:
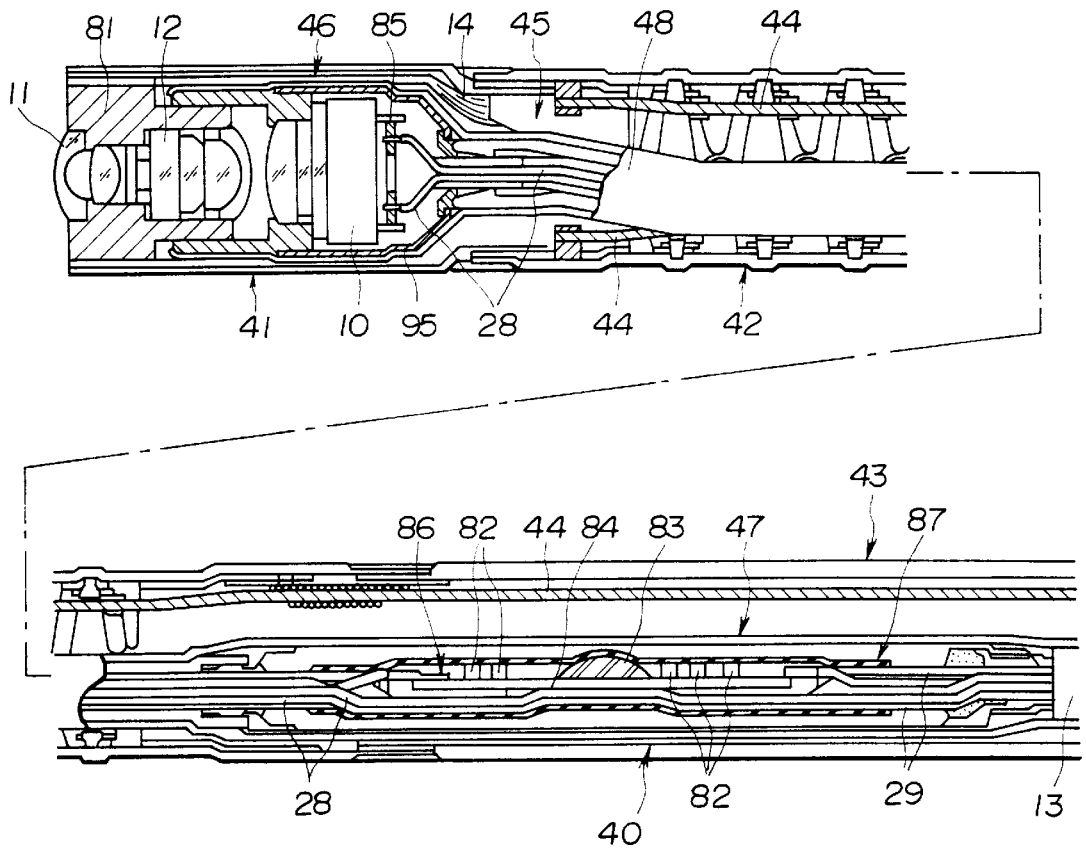
FIGS. 16 and 17 relate to the eighth embodiment of the present invention.
Figure 17:
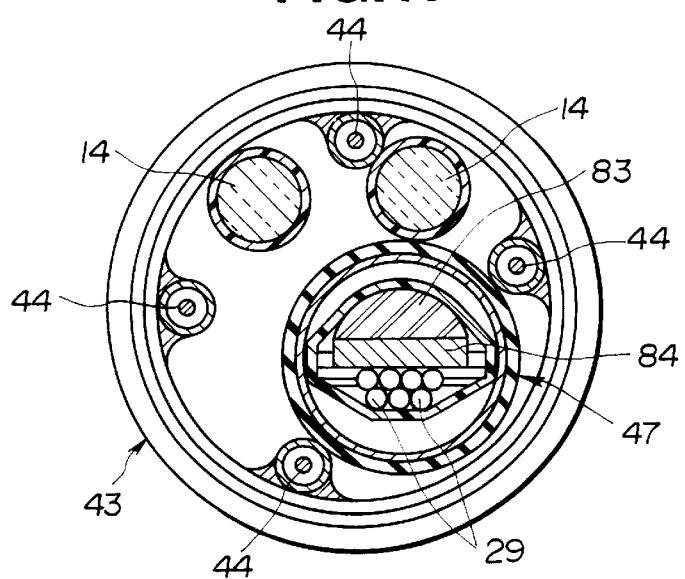

Referring to FIGS. 16 and 17, the eighth embodiment of the present invention will be described.

As shown in FIG. 16, the insertional part 40 comprises the distal structure 41 and proximal rigid unit 43. The distal structure 41 and proximal rigid unit 43 are joined mutually with the bending section 42 between them. The proximal end of the proximal rigid unit 43 is joined with an operation unit via a flexible tube or rigid tube that is not shown.

The imaging unit 45 is incorporated in the insertional part 40. In the imaging unit 45, the distal unit part 46 composed of the objective optical system 12 and CCD 10 is stowed in the distal rigid unit 41, and the back unit part 47 for transmitting an electric signal, which results from photo-electric conversion performed by the CCD 10 and is processed by a signal processor, is stowed in the proximal rigid unit 43.

As shown in FIG. 17, the light guides 14 are placed around the back unit part 47 within the proximal rigid unit 43. The distal portions of the light guides 14 reach the distal surface of a distal structure 81. The proximal portions of the light guides 14 are passed through the proximal rigid unit 43, routed to the universal cord 23 via the operation unit, and then coupled to the light source unit 7.

A signal processor printed-circuit board 84 on which electric parts 82 serving as circuit elements and an IC 83, which process a signal sent from the CCD 10, are mounted is incorporated in the back unit part 47. These circuit-element electric parts 82 are linked to the CCD 10 at a junction 85 by the plurality of signal lines 23 constituting the connection cable 48 lying through the bending section 42.

The proximal ends of the plurality of signal lines 28 constituting the connection cable 48 are coupled to a printed-circuit board 84 at a junction 86. The plurality of signal lines 29 constituting the signal cable 13 are coupled to the proximal end of the printed-circuit board 84.

The light guides 14 lie through the proximal rigid unit 43. The four angle wires 44 passing through the bending section 42 composed of bending tops that are combined rotatably is also placed in the proximal rigid unit 43. The back unit part 47 is stowed away from the inner wall of the proximal rigid unit 43 in the proximal rigid unit 43, and thus separated from the light guides 14, four angle wires 44, and other contents. The back unit part 47 is therefore freely movable in the axial direction of the proximal rigid unit 43 within the proximal rigid unit 43 of the insertional part 40.

In the foregoing structure, when the bending section 42 is angled by advancing or withdrawing the angle wires 44, the signal lines 28 constituting the connection cable 48 stowed in the bending section 42 move in the longitudinal direction of the insertional part 40 in company with the CCD 10 fixed to the distal structure 81.

The back unit part 47, which is not fixed to the proximal rigid unit 43, moves in the longitudinal direction of the insertional part 40 along with the movement of the plurality of signal lines 28.

As mentioned above, in this embodiment, when the bending section of an electronic endoscope is angled, a back unit part stowed in a proximal rigid unit moves with the movement of a plurality of signal lines constituting a connection cable lying through the bending section. A stress working on a junction between a CCD and the signal lines or between the signal lines and a printed-circuit board is therefore alleviated. This result in improved durability against angling.

In the foregoing structure, a movement of the back unit part in a radial direction of an insertional part is not restrained. The back unit part can therefore move not only in the longitudinal direction of the insertional part but also in the radial direction thereof. This means that the back unit part enjoys great freedom. Even if a bending angle is large, a stress to a junction can be alleviated.

Referring to FIGS. 18 and 19, the ninth embodiment of the present invention will be described.

Members having the same structures and effects as those in the eighth embodiment will be assigned the same reference numerals. The description of the members will be omitted.

The signal lines 29 constituting the signal cable 13 are bundled and sheathed with the shield line 13a. The signal lines 29 are then covered with a skin 91 and coupled to the CCU 4. The back unit part 47 is insulated together with the junction 86 between the signal lines 28 and printed-circuit board 84 and the junction 87 between the signal lines 29 and printed-circuit board 84 by means of an insulation tube 92 that is a thermo-contractive tube or the like, and then stowed in a shield pipe 93. Any kind of pipe may be used as the shield pipe 93 as long as it is conductive. For example, a metallic pipe made of brass or stainless steel will do. For improving the conductivity of the shield pipe 93, the pipe may be plated with nickel or the like. A plastic pipe may be used instead of the metallic pipe. In this case, the inner or outer circumference of the plastic pipe is plated or painted with a conductive material.

A pipe lock member 93b is fixed to the back end of the shield pipe 93. The shield pipe 93 is electrically coupled to the shield line 13a shielding the signal lines 29 via the pipe lock member 93b in a gapless manner. A pipe lock member 93a is fixed to the distal end of the shield pipe 93. The shield pipe 93 is electrically coupled to a shield sleeve 94 shielding the plurality of signal lines 28 via the pipe lock member 93a.

The shield sleeve 94 is made by braiding thin conductive lines that are copper wires or fibers plated with tin or silver. The shield sleeve 94 is therefore flexible. The distal end of the shield sleeve 94 is joined with a frame 95, which is shown in FIG. 16, for encapsulating the CCD 10 stowed in the distal structure 81. The shield pipe 93 may be joined directly with the shield line 13a and shield sleeve 94 respectively.

The signal lines 28 and 29 coupled to the distal and back ends of the printed-circuit board 84 situated in the back unit part 47 are secured with an adhesive 96 at the pipe lock members 93a and 93b fixed to the shield pipe 93, thus preventing application of a stress to the the junction 86 between the signal lines 28 and printed-circuit board 84 or the junction 82 between the signal lines 29 and printed-circuit board 84.

The outer circumferences of the shield sleeve 94 and shield pipe 93 are covered with an insulation tube member 97 so that the shield sleeve 94 and shield pipe 93 can be insulated from a main body of an electronic endoscope. At least the portion of the insulating tube member 97 covering the shield sleeve 94 is formed with a flexible tube member.

The shield pipe 93 may not be used. That is to say, the shield sleeve 94 may be extended to the back end of the back unit part 47 and directly joined with the shield line 13a.

The electric parts 82 to be mounted on the printed-circuit board 84; such as, the IC 83, resistors, and capacitors, the junction 86 between the signal lines 28 and printed-circuit board 84, and the junction 87 between the signal lines 29 and printed-circuit board 84 are arranged on one side of the printed-circuit board 84. Signal lines 98 coupled directly to the CCD 10 and included in the signal lines 29 coupled to the CCU 4 are passed along the other side or back side of the printed-circuit board 84 within the shield pipe 93, bundled together with the signal lines 28, routed through the bending section 42, and then coupled to the CCD 10.

According to the foregoing structure, the signal lines 28 and back unit part 47 are covered with a shield and coupled with each other electrically. The shield is then joined with the shield line 13a covering the signal lines 29, whereby a shield protecting almost all the length of the circuitry is realized.

As mentioned above, this embodiment not only has the same advantages as the eighth embodiment but also is effective in reducing noises radiating from a bending section and suppressing influence of external noises.

When the frame 95 encapsulating the CCD 10 is made of a conductive material, the shielding effect of the frame 95 can be upgraded.

The signal lines 28 and 29 are locked by the pipe lock members 93a and 93b attached to both ends of the shield pipe 93 respectively. The movements in an axial direction of the insertional part of the signal lines 28 in relation to angling are conveyed directly to the signal lines 29 via the shield pipe 93. In this embodiment, therefore, no stress is applied to the junction 85 between the printed-circuit board 84 stowed in the shield pipe 93 and the signal lines 28 or the junction 86 between the printed-circuit board 84 and signal lines 29. This results in the improved durability against angling.

The shield pipe 93 not only shields the junction between the signal lines and electric parts but also protects the back unit part 47 from external force.

The signal lines 98 linking the CCU 4 and CCD 10 are passed through a surface of the printed-circuit board 84 opposite to the surface thereof on which the electric parts are mounted, and routed through a dead space within the shield pipe 93 in which the back unit part 47 is stowed. This structure contributes to a decrease in diameter of the shield pipe 93.

The bared signal lines 98 are stowed in the shield pipe 93, and bundled together with the signal lines 28 or 29 by means of the pipe lock member 93a or 93b fixed to each end of the shield pipe. The durabilities of the signal lines are enhanced.

Figure 20:
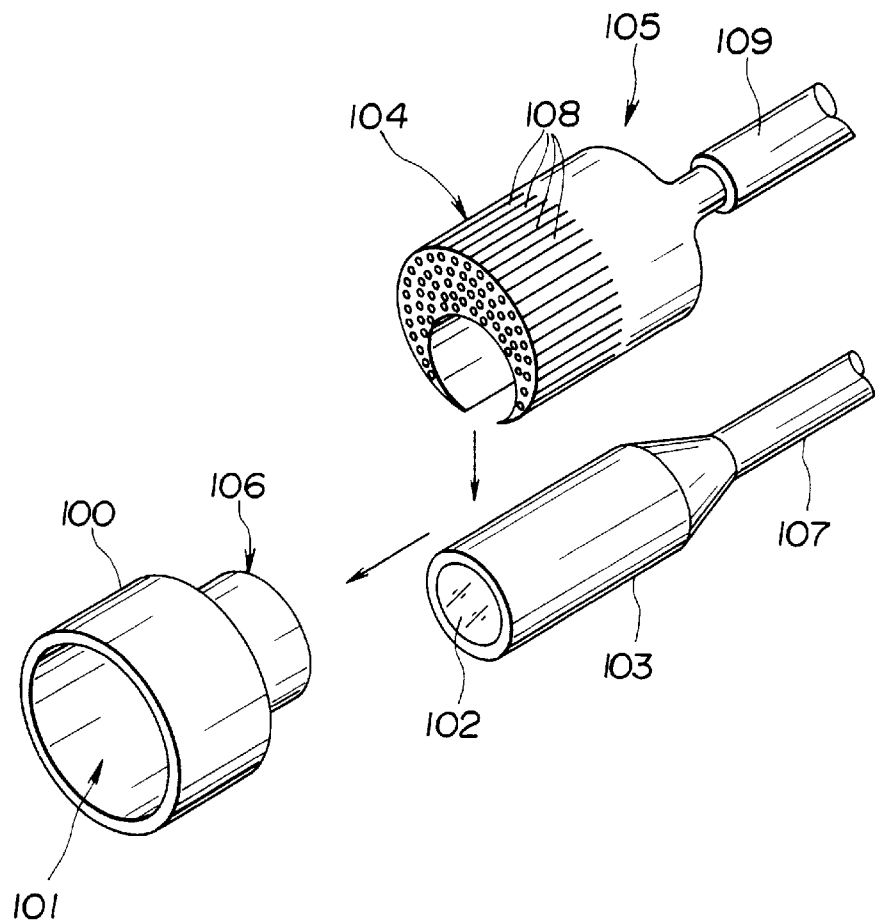
FIGS. 20 to 22 relate to the tenth embodiment of the present invention.
Figure 21:
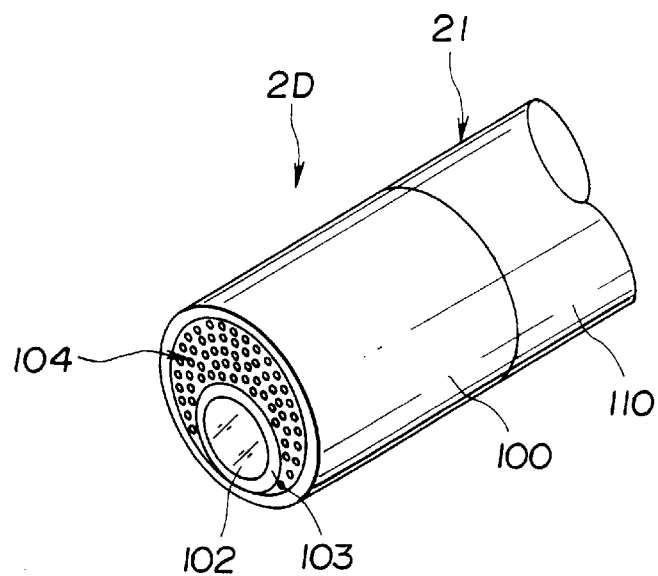
Figure 22:
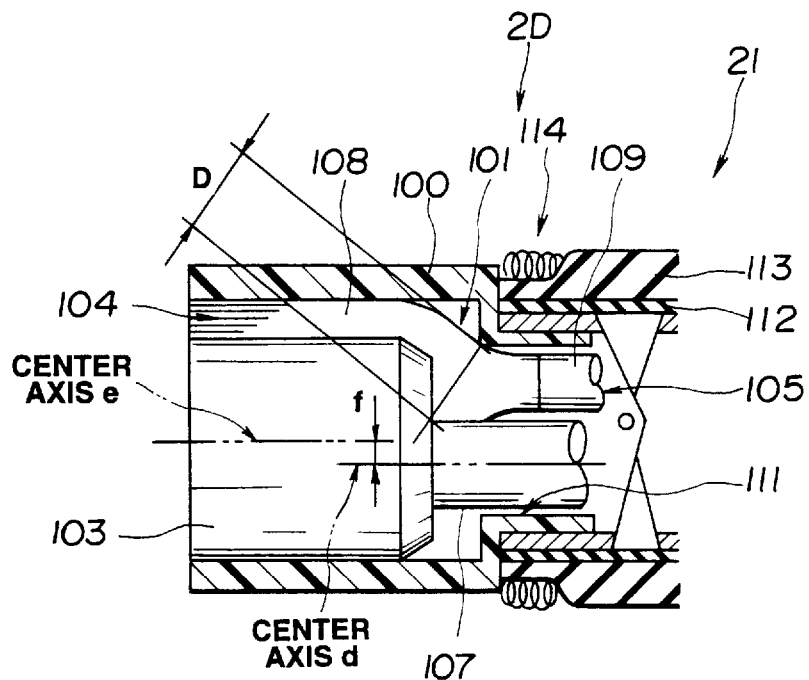

Referring to FIGS. 20 to 22, the tenth embodiment of the present invention will be described.

As shown in FIG. 20, a light guide bundle 105 comprising an imaging unit 103 into which an objective optical system 102, objective lens frame member, CCD, and printed-circuit board are integrated, and a distal light guide part 104 whose cross section is shaped substantially like a crescent in line with the outer circumference of the imaging unit 103 is locked in a hollow 101 of a distal structure 100 constituting the distal portion of an electronic endoscope.

A step 106 to which a bending section that will be described later is coupled and fixed is formed at the proximal end of the distal structure 100.

A signal cable 107 is extending from the back end of the imaging unit 103. The center axis of the signal cable 107 extending from the back end of the imaging unit is deviated from the center axis of the imaging unit 103.

The distal light guide part 104 serving as the distal portion of the light guide bundle 105 is made by attaching a plurality of light guide wires 108 using an adhesive in such a way that the plurality of light guide wires 103 will enclose the imaging unit 103. The distal light guide part 104 is tapered toward the hollow of the step 106 of the distal structure 100. The light guide wires 108 arranged to taper the distal light guide part 104 are sheathed with a silicon tube 109, and thus protected from being broken.

The procedure of stowing the imaging unit 103 and light guide bundle 105 in the distal structure 100 will be described.

To begin with, the outer circumference of the imaging unit 103 is covered with the distal light guide part 104 of the light guide bundle 105. At this time, the distal light guide part 104 is placed on the outer surface of the imaging unit 103 so that the center axis of the signal cable 107 extending from the imaging unit 103 will be positioned farthest.

The imaging unit 103 capped with the distal light guide part 104 is then fitted in the hollow 101 of the distal structure 100. A bending section 110 is joined with the step 106 of the distal structure 100. Thus, the insertional part 21 of an electronic endoscope 2D is constructed as shown in FIG. 21.

The center axis d of the signal cable 107 extending from the back end of the imaging unit 103 fitted in the hollow 101 of the distal structure 100 of the electronic endoscope 2D is, as shown in FIG. 22, deviated by a distance f from the center axis e of the imaging unit 103.

Figure 2:
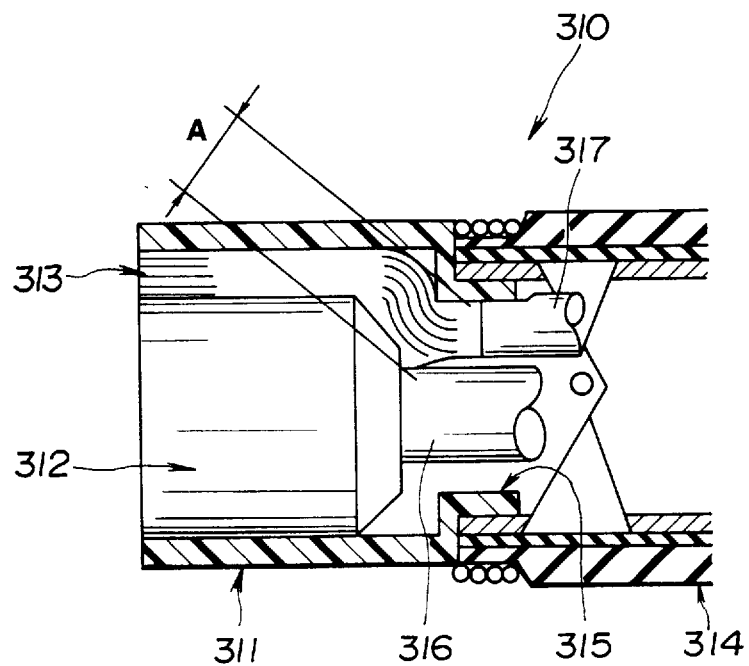

A space D created between a junction 111 between the step 106 of the distal structure 100 and the distal portion of the bending section 110 and the signal cable 107 extending from the imaging unit 103 becomes wider by the deviation of the center axis d from the center axis e than the space A shown in FIG. 2 in which the center axis d of the signal cable 107 is aligned with the center axis e of the imaging unit 103.

The portion of the light guide bundle 105 enclosing the imaging unit 103, which is sheathed with the silicon tube 109, is situated in the space D created between the junction 111 and signal cable 107 with a sufficient clearance preserved.

A braided tube 112 and rubber-made skin 113 constituting the bending section 110 are joined with the step 106 of the distal structure 100. A bobbin winder type lock 114 is formed on the outer circumference of the skin 113, whereby the bending section 110 is fixed to the distal structure 100.

As mentioned above, the center axis of a signal cable extending from the back end of an imaging unit is deviated from the center axis of the imaging unit. A space created between a junction between a distal structure and bending section and a signal cable can be made wider without the necessity of increasing the diameter of the distal structure of an electronic endoscope.

A light guide bundle placed along the outer circumference of the imaging unit is passed through the widened space, and then routed to the proximal portion of the endoscope. Since there is a clearance in a silicon tube, an electronic endoscope in which any of light guide wires will not be broken due to repetitive angling can be provided.

The distal portion of the bending section is coupled and fixed to a step of the distal structure. The outer diameter of a junction between the distal structure and bending section will not become larger than that of the distal structure.

The light guide bundle need not always be arranged to have a cross section shaped substantially like a crescent and to enclose the imaging unit, but may be arranged like a cylinder. Alternatively, a plurality of cylindrical light guide bundles may be arranged around the imaging unit.

Otherwise, a cylindrical protective member may be placed as a light guide protector along the outer circumference of a light guide.

Figure 23:
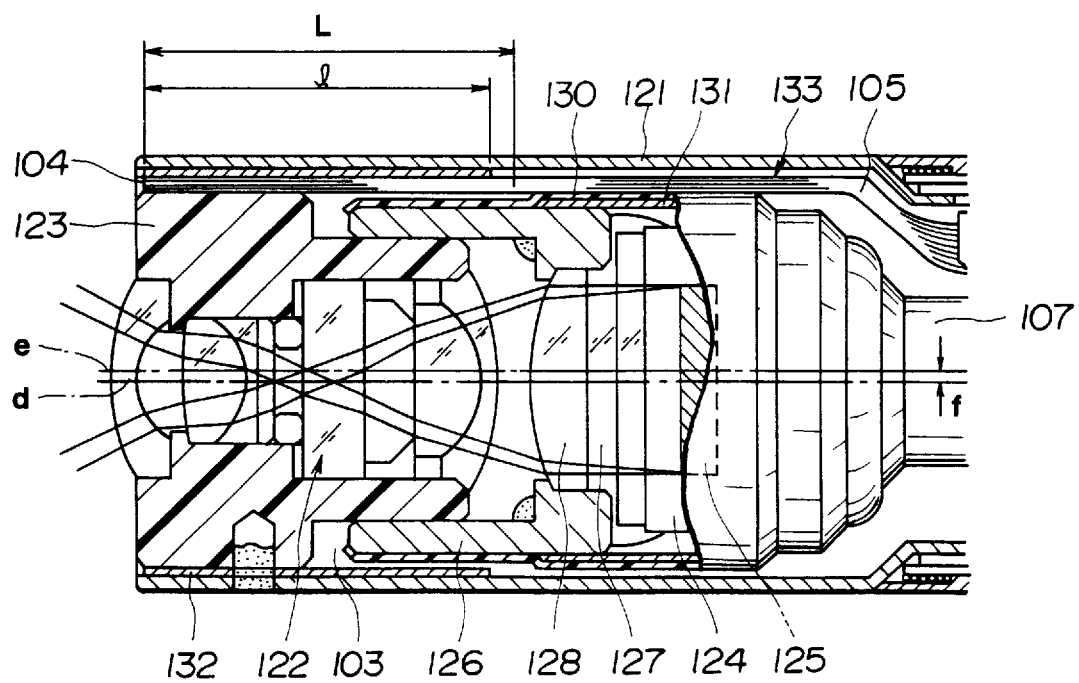
FIG. 23 is a sectional view showing a relationship between a distal structure and an imaging unit in a distal portion of an electronic endoscope in accordance with the eleventh embodiment of the present invention.

Referring to FIG. 23, the eleventh embodiment of the present invention will be described.

As illustrated, the imaging unit 103 placed in a distal structure 121 formed with a conducting member according to this embodiment comprises a lens frame 123 in which a group of optical lenses 122 are locked and which is formed with an insulating member, and an imaging frame 126 to which a crystal lens 127 and field lens 128 are attached using an adhesive so that the optical axes of the crystal lens 127 and field lens 128 will be aligned with the one of a CCD bare chip 125 stowed in a CCD package 124. The outer circumference of the imaging frame 126 is covered with an insulation tube 130 that is a thermo-contractive tube. The light guide bundle 105 having the distal light guide part 104 whose cross section is shaped substantially like a crescent and enclosing the imaging unit 103 is stowed in the distal structure 121.

As mentioned above, the lens frame 123 is formed with an insulating member. If high-frequency current should flow from an electric cautery or the like into the metallic distal structure 121 or lens frame 128, since the lens frame 123 and insulation tube 130 are formed with insulating members, the high-frequency current will not reach the CCD 125.

When the lens frame 123 is formed with a metallic member, the imaging frame 126 is formed with an insulating member but not with a metallic member. Thus, if high-frequency current should flow from an electric cautery or the like into the distal structure 121 or lens frame 123, the high-frequency current will not reach the CCD 125.

The imaging unit 103 is made by fitting the lens frame 123 into the imaging frame 126, joining a shield pipe 131 with the back end of the imaging frame 126, and sheathing the imaging frame 126 and shield pipe 131 with the insulation tube 130. The portion of the imaging unit 103 in which the three members of the imaging frame 126, shield pipe 131, and insulation tube 130 overlap one another has the largest outer diameter. Incidentally, the outer diameter of the lens frame 123 is substantially identical to that of the insulation tube 130.

The distal light guide part 104 that is made rigid due to an adhesive and constitutes the light guide bundle 105 enclosing the imaging unit 103 is shielded with a light guide base 132 having a length 1. When the distal light guide part 104 is structured by attaching wires using an adhesive, if the adhesive oozes out, the rigid part of the light guide bundle 105 becomes too long. The outer diameter of the insulation tube 130 covering the imaging frame 126 and shield pipe 131 may be varied due to a sag occurring in the course of contraction. Consequently, the outer diameter of the portion of the imaging unit covered with the back part of the shield pipe may become too large.

When the imaging unit 103 including the distal light guide part 104 whose cross section is shaped like a crescent is fitted in the distal structure 121, the portion of the light guide bundle 105 that should be soft becomes rigid. Moreover, the outer diameter of the portion of the imaging unit 103 covered with the back part of the shield pipe becomes too large. Consequently, the light guide wires 108 that have become rigid may not be stowed in the distal structure. Eventually, the distal portion of an endoscope may not be constructed.

The length of the rigid part of the distal light guide part 104 structured using an adhesive is set to the same value as a length L from the distal end of the distal light guide part to a point preceding the portion of the imaging unit 103 in which the outer diameter of the imaging unit 103 becomes largest and the three members of the imaging frame 126, shield pipe 131, and insulation tube 103 overlap one another.

Thus, if the outer diameter of the insulation tube 130 covering the shield pipe that has been contracted is varied, since the light guide wires 108 constituting the light guide bundle 105 to be situated within the insulation tube 130 are not solidified using an adhesive, the light guide bundle 105 can be situated effortlessly owing to a gap 133 whose width is equal to the thickness of the light guide base 132.

In the present invention, it will be apparent that a wide range of different embodiments can be formed on the basis of the invention without a departure from the spirit or scope of the invention. This invention will be limited to the appended claims but not restricted to any specific embodiments.

What is claimed is:

1. An electronic endoscope, comprising:

an insertional part, for inserting into a human body cavity, at least part of whose armor is formed with a conducting member;

an imaging means incorporated in said insertional part and realized with a solid-state imaging device;

a signal transmitting means for transmitting an electric signal resulting from photoelectric conversion performed by said solid-state imaging device; and a signal processing means for transforming said electric signal transmitted by said signal transmitting means into a video signal;

said conducting member, exposed to said human body cavity, serving as said armor of said insertional part being electrically isolated from said imagingmeans, signal transmitting means, and signal processing means, wherein said conducting member is isolated from ground;

further including shield means for covering outer peripheries of said imaging means and signal transmitting means, wherein said shield means include an armor which is sheathed with an insulating means for insulating said shield means.

2. An electronic endoscope, comprising:

an insertional part, for inserting into a human body cavity, whose armor is formed with a conducting member, wherein said conducting member is isolated from ground;

an imaging means incorporated in said insertional part and realized with a solid-state imaging device;

a signal transmitting means for transmitting an electric signal resulting from photoelectric conversion performed by said imaging means;

a signal processing means for transforming said electric signal transmitted by said signal transmitting means into a video signal;

a shield means for shielding said imaging means and signal transmitting means; and an insulating means, exposed to said human body cavity, for covering an outer periphery of said shield means.

3. An electronic endoscope, comprising:

an insertional part whose armor is at least in part formed with a conducting member which is isolated from ground, for inserting into a human body cavity, composed of a distal rigid unit stowing an imaging means realized with a solid-state imaging device, a proximal rigid unit stowing at least some of electric parts that constitute a signal processor for said imaging means, and a bending section lying between said distal rigid unit and proximal rigid unit and stowing a connection cable that links said imaging means and electric parts;

a signal transmitting means for transmitting an electric signal from said at least some electric parts resulting from photoelectric conversion performed by said imaging means;

a signal processing means for transforming an electric signal transmitted by said signal transmitting means into a video signal;

a shield means for shielding said solid-state imaging device, connection cable, signal processor, and signal transmitting means; and an insulating means, exposed to said human body cavity, for covering an outer periphery of said shield means.

4. An electronic endoscope according to claim 1, further comprising a power supply means for supplying power to said signal processing means, wherein said signal processing means and power supply means are insulated from each other.

5. An electronic endoscope according to claims 1, 2 or 3, wherein said shield means is electrically coupled to a ground in said signal processing means.

6. An electronic endoscope according to claims 1, 2, or 3, further including a grip joined with the proximal end of said insertional part, wherein said grip includes an armor formed with an insulating member.

7. An electronic endoscope according to claims 1, 2 or 3, wherein said insulating means is a thermo-contractive tube.

8. An electronic endoscope according to claim 2 or 3, further comprising a power supply means for supplying power to said signal processing means, wherein conducting means serving as an armor of said insertional part and said signal processing means are insulated from each other, said signal processing means and power supply means are insulated from each other.

9. An electronic endoscope according to claim 2 or 3, wherein an outer periphery of a conducting member serving as an armor of said insertional part is covered with an insulation layer.

10. An electronic endoscope according to claim 2, wherein an objective optical system opposed to an imaging surface of said imaging means is composed of a lens frame member holding optical lenses and a locking frame member fixed to said shield means, and said lens frame member is formed with an insulating member.

11. An electronic endoscope according to claim 10, wherein said lens frame member formed with an insulating member overlaps an end of a thermo-contractive tube serving as said insulating means.

12. An electronic endoscope according to claim 3, wherein an objective optical system opposed to an imaging surface of said imaging means is composed of a lens frame member holding optical lenses and a locking frame member fixed to said shield means, and said locking frame member is formed with an insulating member.

13. An electronic endoscope according to claim 12, wherein said locking frame member formed with an insulating member overlaps an end of a thermo-contractive tube serving as said insulating means.

14. An electronic endoscope according to claim 3, further comprising: a signal processor printed-circuit board lying between said imaging means and signal processing means, containing plurality of terminals, wherein said signal transmitting means includes center conductors and outer conductors, wherein said center conductors are attached to said plurality of terminals, and wherein said electric parts are interconnected and mounted; and a holder that is equalized in potential with said outer conductors of said signal transmitting means and is in contact with or adjacent to said signal processor printed-circuit board, wherein said terminals on said signal processor printed-circuit board are spatially separated from ends of said outer conductors of said signal transmitting means.

15. An electronic endoscope according to claim 14, wherein said terminals on said signal processor printed-circuit board are separated from a position at which said holder is in contact with or adjacent to said signal processor printed-circuit board, and said terminals and said ends of said outer conductors are spatially separated from each other.

16. An electronic endosdope according to claim 14, wherein a ditch is formed on one side of said signal processor printed-circuit board or holder on which said holder is in contact with or adjacent to said signal processor printed-circuit board, and wherein said terminals on said signal processor printed-circuit board and said ends of said outer conductors of said signal transmitting means are spatially separated from each other.

17. An electronic endoscope according to claim 16, wherein said holder includes margins.

18. An electronic endoscope according to claim 14, wherein said electric signal comprises video signals and said plurality of terminals include a video signal input terminal and a video signal output terminal to which some of said center conductors are attached, and wherein said video signal input terminal and a video signal output terminal are separate from the remaining of said plurality of terminals.

19. An electronic endoscope according to claim 18, wherein a signal processing IC made out of electric parts interconnected and mounted on said signal processor printed-circuit board is separated from the remaining of said plurality of terminals, said video signal input terminal and video signal output terminal are arranged near said signal processing IC.

20. An electronic endoscope according to claim 3, wherein said at least some electric parts arranged in said proximal rigid unit are freely movable at least in a longitudinal direction of said insertional part of said electronic endoscope.

21. An electronic endoscope according to claim 20, wherein said connection cable coupled to said image means in said distal rigid unit and routed through said bending section is sheathed with at least a portion of said shield means having flexibility at least within said bending section.

22. An electronic endoscope according to claim 20, wherein said at least some electric parts disposed in said proximal rigid unit are stowed in a protective member.

23. An electronic endoscope according to claim 22, wherein said protective member is formed with a conducting member.

24. An electronic endoscope according to claim 22 or 23, wherein said signal transmitting means includes signal lines which directly link said signal processing means and said imaging means, said signal lines being routed through said protective member.

25. An electronic endoscope according to claim 20, wherein a shield frame that stows and shields said electric parts is incorporated in said insertional part, wherein said connection cable links said imaging means situated in said distal rigid unit of said insertional part and portions of said at least some electric parts, and wherein said connection cable and said signal transmitting means are fixed to both ends of said shield frame by locking means.

26. An electronic endoscope according to claim 25, wherein a plurality of signal lines constituting said signal transmitting means are sheathed all together with a general shield member that is electrically coupled to said shield frame.

* * * * *